United States Patent
Lim et al.

(10) Patent No.: US 7,566,325 B2
(45) Date of Patent: *Jul. 28, 2009

(54) WINGED MEDICAL NEEDLE DEVICE

(75) Inventors: Kah Hock Lim, Singapore (SG); Boon Tong Low, Singapore (SG); Chek Lon Yang, Singapore (SG); Ai Ling Teo, Singapore (SG)

(73) Assignee: JMS Co., Ltd., Hiroshima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/075,704

(22) Filed: Mar. 13, 2008

(65) Prior Publication Data
US 2008/0167627 A1  Jul. 10, 2008

Related U.S. Application Data

(63) Continuation of application No. 10/938,341, filed on Sep. 9, 2004, now Pat. No. 7,367,962.

(51) Int. Cl.
*A61M 5/00* (2006.01)
*A61M 5/32* (2006.01)

(52) U.S. Cl. ..................... 604/198; 604/263

(58) Field of Classification Search ............... 604/110, 604/163, 263, 171, 192–198, 177, 158, 164.08, 604/181, 187, 919
See application file for complete search history.

(56) References Cited

U.S. PATENT DOCUMENTS

| 5,088,982 | A | 2/1992 | Ryan |
| 7,322,963 | B2 * | 1/2008 | Goh ............... 604/165.03 |
| 7,367,962 | B2 * | 5/2008 | Lim et al. ............... 604/198 |
| 2005/0234408 | A1 | 10/2005 | Chong et al. |

FOREIGN PATENT DOCUMENTS

| JP | 1-212561 | 8/1989 |
| WO | 91/04761 | 4/1991 |
| WO | 03/033055 | 4/2003 |
| WO | WO 03033055 A * | 4/2003 |

* cited by examiner

*Primary Examiner*—Matthew F Desanto
(74) *Attorney, Agent, or Firm*—Hamre, Schumann, Mueller & Larson, P.C.

(57) ABSTRACT

The configuration of the present invention includes a winged shield that has a cylindrical shield tube and wings linked to a front end side of the shield tube, a hub that is inserted into an inner bore of the shield tube so as to be movable in an axial direction, and a cannula that is mounted to a front end portion of the hub. By engaging a protrusion with a third annular groove, the hub is held with the winged shield in a state where the cannula protrudes for a predetermined length from a front end of the shield tube. In a state where an inward annular protrusion of the shield tube is engaged with a first holding portion, a tip of the cannula can be stored in the shield tube. By engaging the protrusion of a holding mechanism with a first annular groove, the hub is held with the shield tube so as not to be moved within the shield tube.

15 Claims, 10 Drawing Sheets

WINGED MEDICAL NEEDLE DEVICE

CROSS REFERENCE TO RELATED APPLICATION

This application is a Continuation of application Ser. No. 10/938,341, filed Sep. 9, 2004, now U.S. Pat. No. 7,367,962, which application is incorporated herein by reference.

BACKGROUND OF THE INVENTION

1. Field of the Invention

The present invention relates to a medical needle device having a winged shield for the prevention of needle-stick injuries, in which a cannula can be stored safely after use.

2. Related Background Art

Conventionally, contamination and infection due to needle-stick injuries from injection needles, puncture needles and the like have been a problem in medical facilities. In particular, recently, as hepatitis B, hepatitis C, HIV (human immunodeficiency virus) and the like have become a widespread social issue, there is a demand for systems that actively prevent the occurrence of accidents such as needle-stick injuries and the like.

As a way to prevent needle-stick injuries, various injection needle devices that have a configuration in which a cannula is covered by a cover when injection needles or puncture needles are collected after use have been proposed. In most cases, such a system for preventing needle-stick injuries has a cylindrical protection cover (hereinafter, referred to as a shield) for preventing needle-stick injuries after use, and the shield can slide with respect to an injection needle. That is, the system is configured so that the injection needle can be either exposed or covered by the shield depending on the sliding state of the shield.

Meanwhile, for measures such as an infusion, a blood transfusion, extracorporeal blood circulation and the like, winged injection needle devices are used widely. Winged injection needle devices have a structure in which wings are mounted to a hub that has a front end at which an injection needle is fastened and a rear end that is connected to an infusion tube. Thus, a system for preventing needle-stick injuries for a winged injection needle device necessitates a special structure. That is, the structure has to be such that the wings do not obstruct the sliding of a shield. Conventional structures for achieving this are categorized into a type in which wings are attached to a cannula or a hub and a type in which wings are attached to a shield.

Examples of the latter structure are described in, for example, JP H06(1994)-7861B, International Publication No. WO 91/04761, or U.S. Pat. No. 5,088,982. In each of these conventional examples, wings are attached to the outer peripheral surface of a slidable cylindrical shield, and the wings slide together with the shield on the outer side of an injection needle. In order to prevent needle-stick injuries after use of the injection needle, the shield is slid so that the tip of the injection needle can be covered.

During a puncturing action using the above-mentioned injection needle device in which the wings are attached to the shield, the shield is held by hand. Therefore, it is required that the injection needle device be provided with a mechanism in which a hub can be held securely with the shield and is integrated with the shield. Furthermore, after the injection needle after use is retracted into the shield so that the tip of a cannula is covered by the shield (after needle storage), it is required that the cannula that has been retracted be held securely in the shield and that this state be maintained securely. On the contrary, during a storing action for retracting the injection needle after use into the shield, a force for holding the hub with respect to the shield rather should be weak.

As described above, it is preferable that the respective holding forces for holding an injection needle with a shield during a puncturing action, during a storing action, and after needle storage be set suitably.

However, in conventional injection needle devices with a winged shield, a common mechanism is used to hold an injection needle during a puncturing action, during a storing action, and after needle storage, and thus the respective holding forces used during the puncturing action, the storing action, and after the needle storage cannot be attained suitably, which has been disadvantageous.

SUMMARY OF THE INVENTION

A winged medical needle device according to the present invention includes a winged shield that has a substantially cylindrical shield tube and a pair of wings linked to a front end side of the shield tube, a hub that is inserted into an inner bore of the shield tube so as to be movable in an axial direction, and a cannula that is mounted to a front end portion of the hub.

The hub includes a main tubular portion, a first holding portion that is provided on a side closer to a front end than the main tubular portion, and a second holding portion that is provided on a side closer to a rear end than the main tubular portion.

The first holding portion includes a first large diameter portion that has a portion whose diameter is larger than a diameter of the main tubular portion, a first annular groove that is provided on a side closer to the front end of the hub than the first large diameter portion, a second annular groove that is provided on a side closer to the rear end than the first large diameter portion, and a second large diameter portion that is provided on a side closer to the rear end than the second annular groove so as to be adjacent to the second annular groove.

The second holding portion includes a third annular groove.

The winged shield includes a holding mechanism that is provided at a base end portion of the shield tube, and an inward annular protrusion that is formed on an inner surface of the shield tube on a side closer to a base end than the holding mechanism. The inward annular protrusion can be engaged with the second annular groove.

The holding mechanism includes a bendable strip that is attached to an outer peripheral surface of the shield tube, a protrusion that is provided on the bendable strip, and a through hole that is provided on a wall of the shield tube so that the protrusion can be inserted into the inner bore of the shield tube by wrapping of the bendable strip. The protrusion can be engaged with the first annular groove and the third annular groove.

By inserting the protrusion into the through hole so that the protrusion is engaged with the third annular groove, the hub is held with the shield tube so as not to be moved within the shield tube in a state where the cannula protrudes for a predetermined length from a front end of the shield tube.

By moving the hub in the axial direction toward the base end with respect to the shield tube, the inward annular protrusion of the shield tube is engaged with the second annular groove of the hub, and a tip of the cannula is stored in the shield tube in this state. Moreover, by engaging the protrusion of the holding mechanism with the first annular groove, the hub is held with the shield tube so as not to be moved within the shield tube.

According to this configuration, the respective holding forces for holding a medical needle with a winged shield during a puncturing action, during a storing action, and after needle storage can be set suitably. Thus, the action of holding a hub securely with a winged shield during a puncturing action, the action of moving a cannula to a storage position after use, and the action of storing the cannula in a position in the winged shield in which needle-stick injuries can be prevented and maintaining this state, can be performed safely and easily.

In the winged medical needle device, preferably, by inserting the protrusion into the through hole so that the protrusion is engaged with the third annular groove, the hub is held so as not to be moved while being rotatable within the shield tube in the state where the cannula protrudes for a predetermined length from the front end of the shield tube.

In the winged medical needle device, preferably, a surface of the protrusion that faces a bottom surface of the third annular groove when the protrusion is engaged with the third annular groove includes a curved surface having a curvature substantially equal to a curvature of the bottom surface.

In the winged medical needle device, preferably, the first large diameter portion has an outer diameter larger than a maximum outer diameter of the second large diameter portion.

In the winged medical needle device, preferably, the holding mechanism further includes a latching structure that allows the bendable strip to be latched to the shield tube.

The latching structure includes, for example, a latching protrusion that is provided on the outer peripheral surface of the shield tube, and a protruding piece portion that is provided on a front end side (side opposite to the side of the bendable strip on which the bendable strip is attached to the outer peripheral surface of the shield tube) of the bendable strip and includes an opening.

In the winged medical needle device, preferably, a surface of the bendable strip that faces an outer surface of the shield tube when the protrusion is engaged with the third annular groove includes a curved surface having a curvature substantially equal to a curvature of the outer surface.

In the winged medical needle device, preferably, a surface of the protrusion that faces a side surface of the first annular groove on a front end side of the first annular groove when the protrusion is engaged with the first annular groove includes a plane surface.

In the winged medical needle device, preferably, a surface of the inward annular protrusion is provided with a rib parallel to the axial direction of the shield tube and a rearward annular protrusion that is arranged on a side closer to the base end than the rib, and the rib has a length in a longitudinal direction that is longer than a width of the third annular groove.

In the winged medical needle device, preferably, the first holding portion further includes a third large diameter portion that is arranged between the first large diameter portion and the second annular groove, and a fourth annular groove that is arranged between the first large diameter portion and the third large diameter portion. The inner surface of the shield tube is provided with an auxiliary holding protrusion. The auxiliary holding protrusion is formed in a position of the inner surface of the shield tube, in which the auxiliary holding protrusion faces the fourth annular groove when positioning between the through hole and the third annular groove is obtained so that the protrusion of the bendable strip can be engaged with the third annular groove.

In the winged medical needle device, preferably, the third large diameter portion has an outer diameter larger than a maximum outer diameter of the second large diameter portion.

Furthermore, preferably, the pair of wings have a thickness that is smaller in a region on a base end side than in a region on a front end side.

Furthermore, preferably, an outer surface of a bottom portion of the shield tube is formed so as to be flat.

Furthermore, preferably, a holding tab is formed on an upper surface of the shield tube.

Furthermore, preferably, the holding tab is formed on at least one selected from a front end portion of the shield tube and a rear end portion of the shield tube.

DETAILED DESCRIPTION OF THE INVENTION

Embodiment 1

Figure 1:
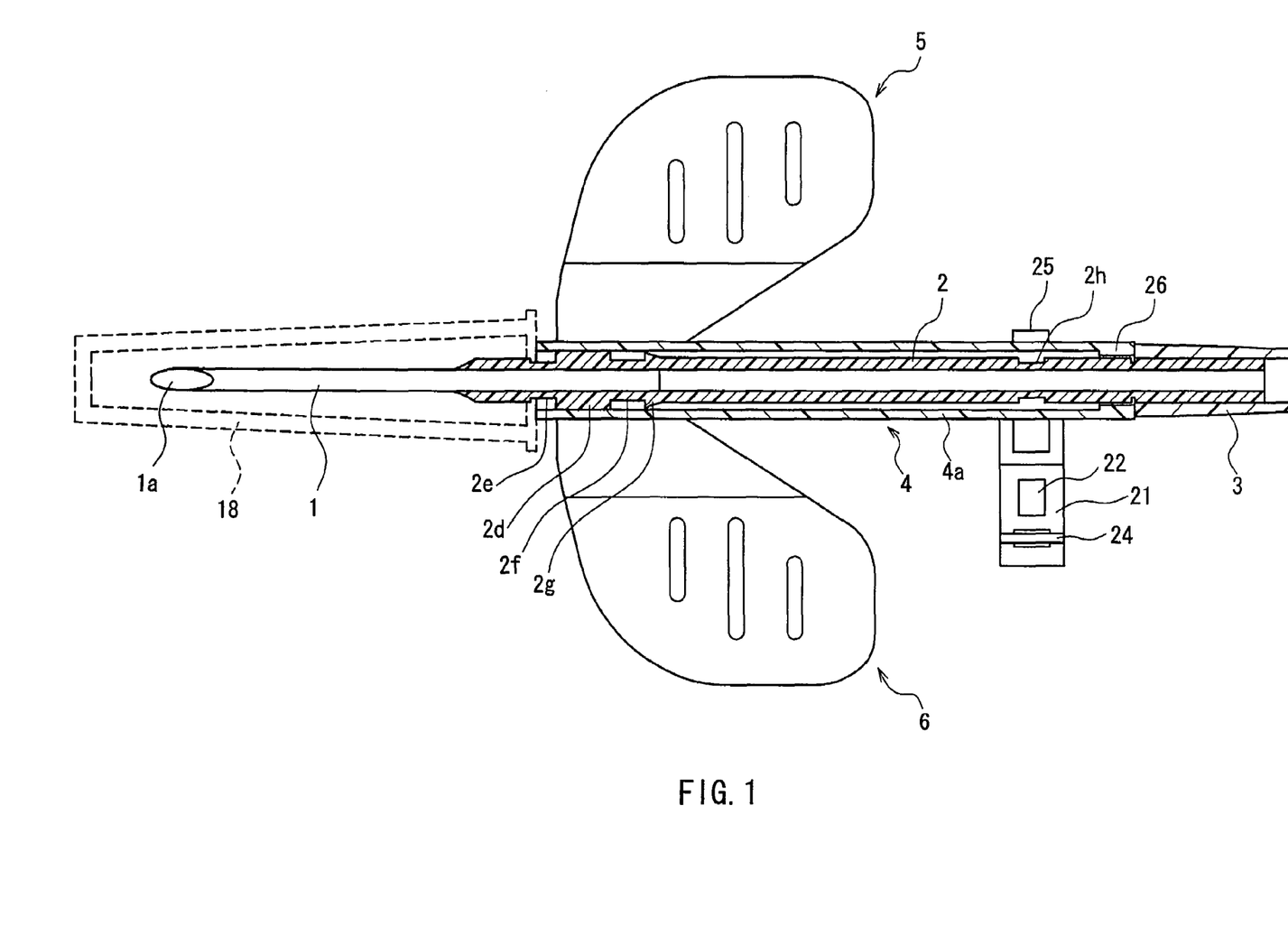
FIG. 1 is a partial cross-sectional view showing the planar shape of a winged medical needle device according to Embodiment 1 of the present invention.

FIG. 1 is a partial cross-sectional view showing the planar shape of a winged medical needle device according to Embodiment 1 of the present invention. Numeral 1 denotes a cannula, which is fastened to the front end portion of a hub 2 made of plastic. A tube 3 is connected to the rear end portion of the hub 2. Numeral 4 denotes a winged shield, which includes a substantially cylindrical shield tube 4a made of plastic, and left and right wings 5 and 6. The hub 2 can be moved in the axial direction in the inner bore of the shield tube 4a, and the cannula 1 can be retracted into the inner bore of the shield tube 4a. The left and right wings 5 and 6 are provided at the front end portion of the shield tube 4a, i.e. at the end portion on the side from which the cannula 1 that has been retracted into the shield tube 4a protrudes. The wings 5 and 6 are linked to both sides of the peripheral surface of the shield tube 4a, and are of symmetric shape with respect to the axis of the shield tube 4a. A needle cap 18 is mounted to the front end portion of the hub 2, covering the cannula 1.

Figure 2:
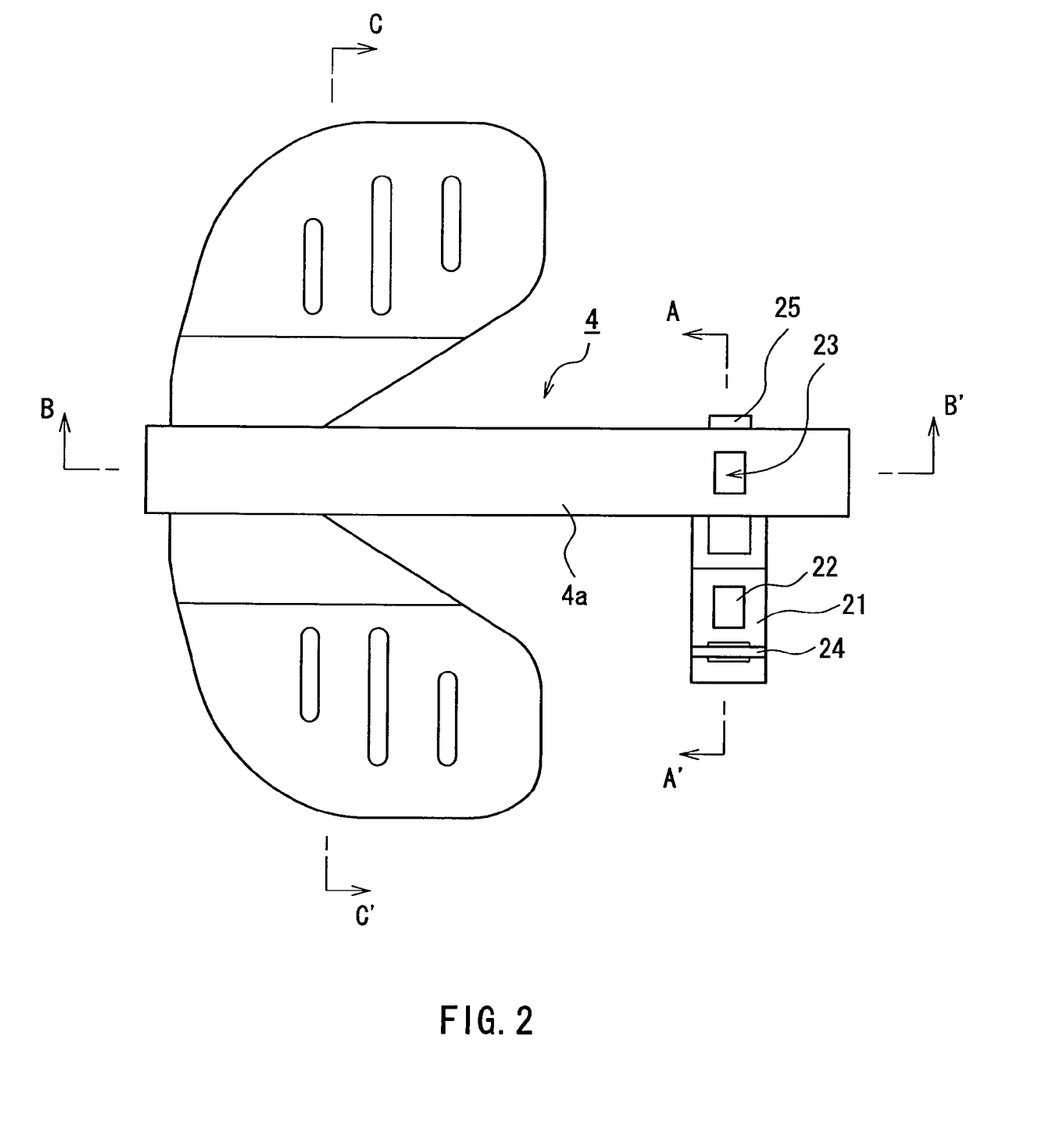
FIG. 2 is a plan view of a winged shield of the winged medical needle device shown in FIG. 1.
Figure 3:
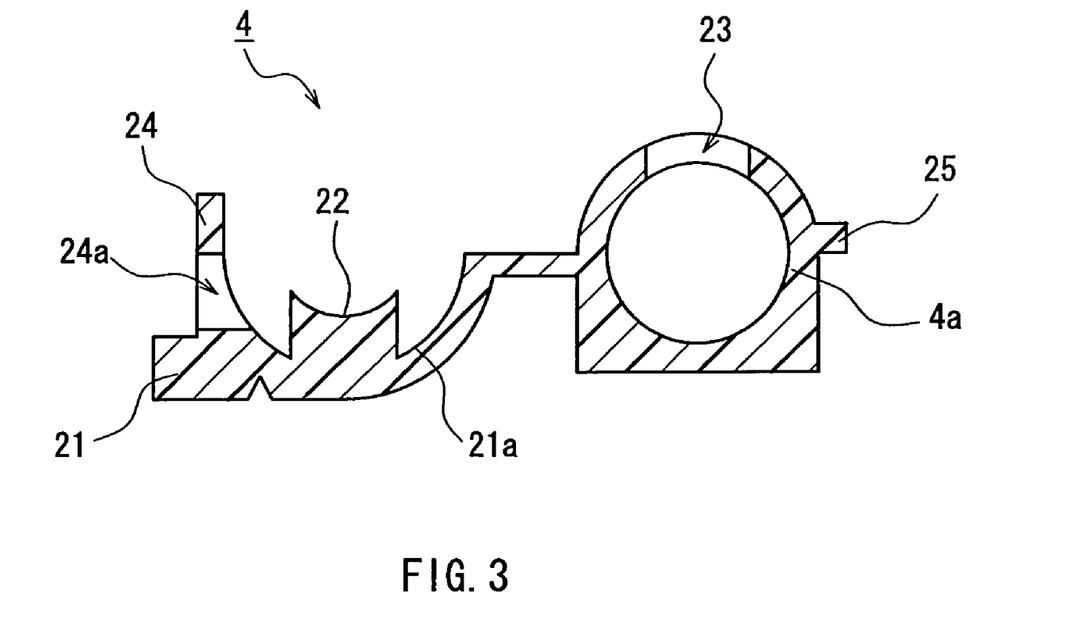
FIG. 3 is an expanded cross-sectional view taken on line A-A' of FIG. 2.

Next, the description is directed to the winged shield 4 with reference to FIGS. 2 to 6. FIG. 2 is a plan view of the winged shield 4, and FIG. 3 is an expanded cross-sectional view taken on line A-A' of FIG. 2.

As shown in FIGS. 2 and 3, the winged shield 4 has a holding mechanism that is provided at the base end portion of the shield tube 4a and includes a bendable strip 21. The bendable strip 21 is fastened to the shield tube 4a on one side in its longitudinal direction. The other side can be wrapped around the axis of the shield tube 4a. A protrusion 22 is provided on the surface of the bendable strip 21 that is to face the outer surface of the shield tube 4a when the bendable strip 21 is wrapped. A through hole 23 is formed on the wall of the shield tube so that the protrusion 22 can be inserted into the inner bore of the shield tube 4a by wrapping of the bendable strip 21. A protruding piece portion 24 having an opening 24a is provided on the front end side of the bendable strip 21, and a latching protrusion 25 to which the protruding piece portion 24 can be latched is provided on the outer peripheral surface of the shield tube. The latching protrusion 25 can be inserted into the opening 24a of the protruding piece portion 24, and the protruding piece portion 24 can be latched to the latching protrusion 25.

Figure 4:
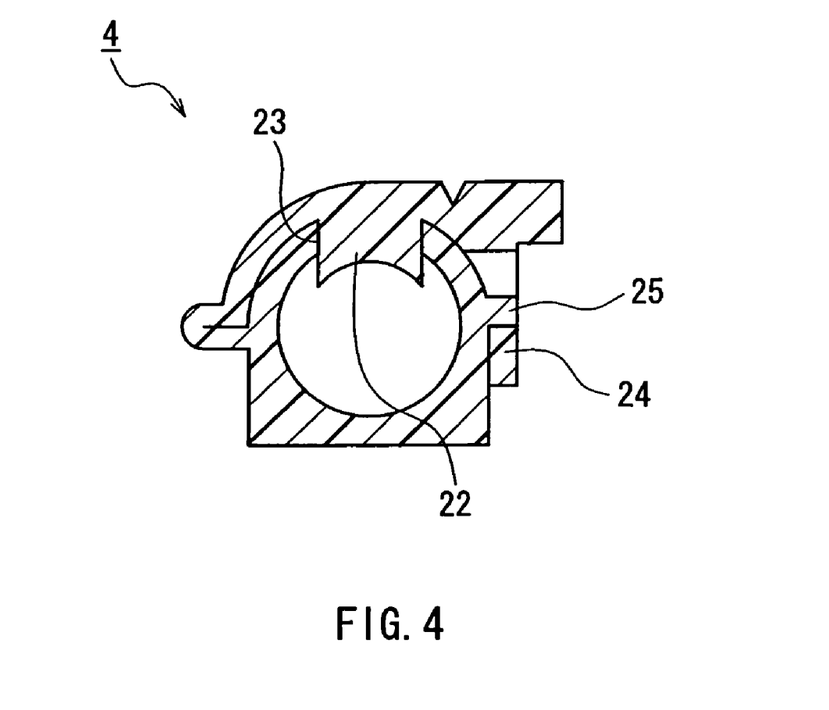
FIG. 4 is a cross-sectional view for explaining the state where a protrusion is inserted into a through hole in the winged shield shown in FIG. 3.

As shown in FIG. 3, preferably, a surface 21a of the bendable strip 21 includes a curved surface having a curvature equal to the curvature of the outer surface of the shield tube 4a that is to face the surface 21a when the protrusion, 22 is inserted into the through hole 23 so as to be engaged with a third annular groove that will be described later. This is preferable because this facilitates a latching action of latching the protruding piece portion 24 to the latching protrusion 25. In order to facilitate the latching action of latching the protruding piece portion 24 to the latching protrusion 25, the curvature of the above-mentioned curved surface of the surface 21a does not have to be exactly the same but is only required to be substantially the same as that of the above-mentioned outer surface of the shield tube 4a. FIG. 4 shows the state where the protrusion 22 is inserted into the through hole 23, and the protruding piece portion 24 is latched to the latching protrusion 25.

Figure 5A:
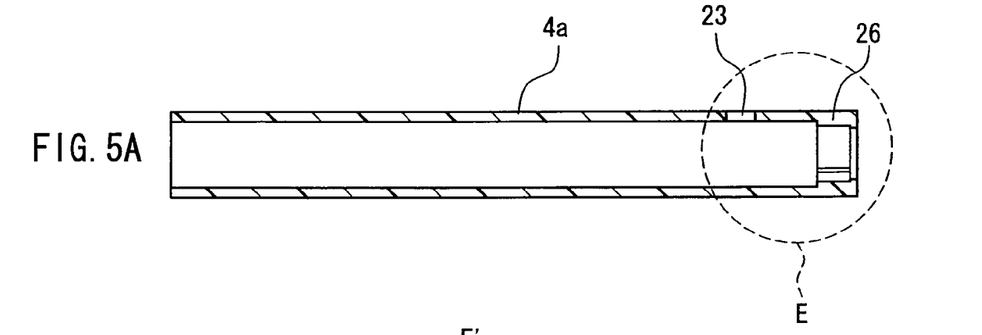
FIG. 5A is a cross-sectional view taken on line B-B' of FIG. 2.
Figure 5B:
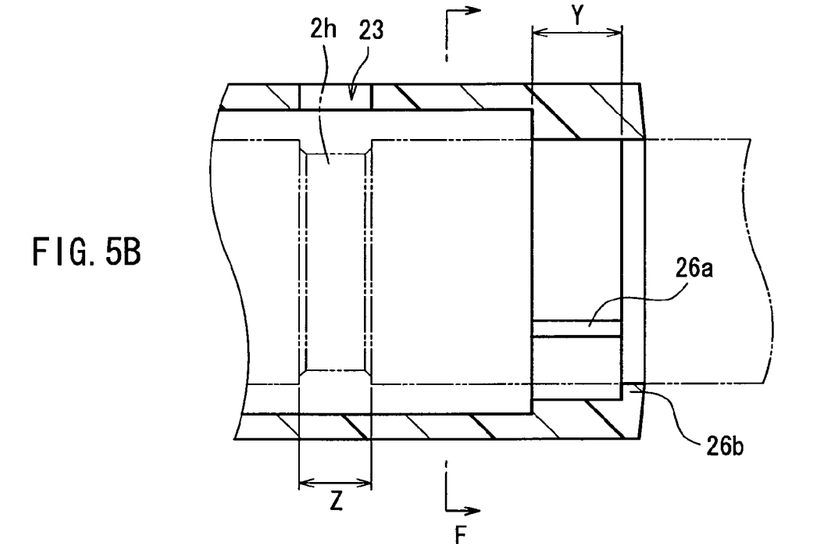
FIG. 5B is an enlarged view of a portion denoted E in FIG. 5A.
Figure 5C:
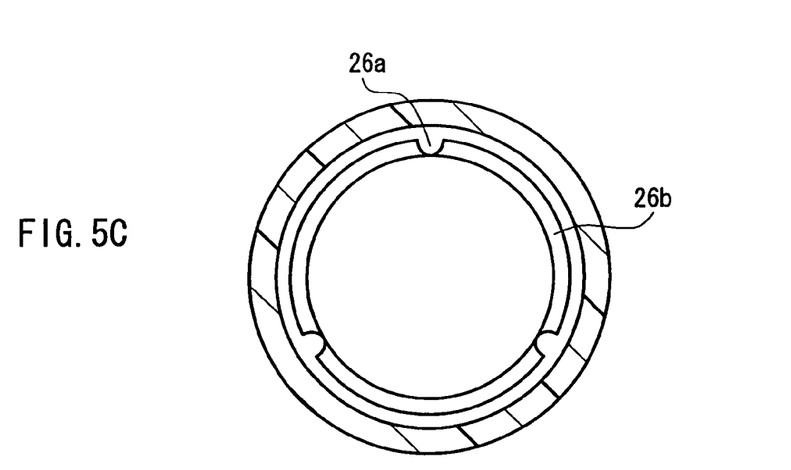
FIG. 5C is a cross-sectional view taken on line F-F' of FIG. 5B.

FIG. 5A is a cross-sectional view taken on line B-B' of FIG. 2, FIG. 5B is an enlarged view of a portion denoted E in FIG. 5A, and FIG. 5C is a cross-sectional view taken on line F-F' of FIG. 5B. As shown in FIG. 5A, an inward annular protrusion 26 is formed on the inner surface of the shield tube 4a on a side even closer to the base end than the holding mechanism. In this figure, numeral 23 denotes the through hole of the holding mechanism. As shown in FIGS. 5B and 5C, the surface of the inward annular protrusion is provided with a rib 26a parallel to the axial direction of the shield tube and a rearward annular protrusion 26b that is arranged on a side closer to the base end than the rib 26a. The inward annular protrusion may have three ribs 26a on its surface, which are arranged at an angle of 120 degrees with respect to each other. The height of the ribs 26a is substantially the same as the height of the rearward annular protrusion 26b, and the surface of the inward annular protrusion at a portion where each of the ribs 26a is joined to the rearward annular protrusion 26b is a plane surface. The rib has a length Y in the longitudinal direction that is longer than a width Z of a third annular groove 2h. Therefore, when the inward annular protrusion 26 passes over the third annular groove 2h, the rearward annular protrusion 26b is not caught by faces of the third annular groove 2h, and a jerky motion is prevented, thereby allowing the shield tube to slide smoothly. It is more preferable that a portion of the surface of the inward annular protrusion 26 on a side closer to the front end than the rearward annular protrusion 26b is slanted, and the shield tube has an inner diameter at a portion in which the inward annular protrusion 26 is provided, which increases from the base end to the front end on the side closer to the front end than the rearward annular protrusion 26b. In this case, the shield tube can be slid more smoothly.

Figure 6:
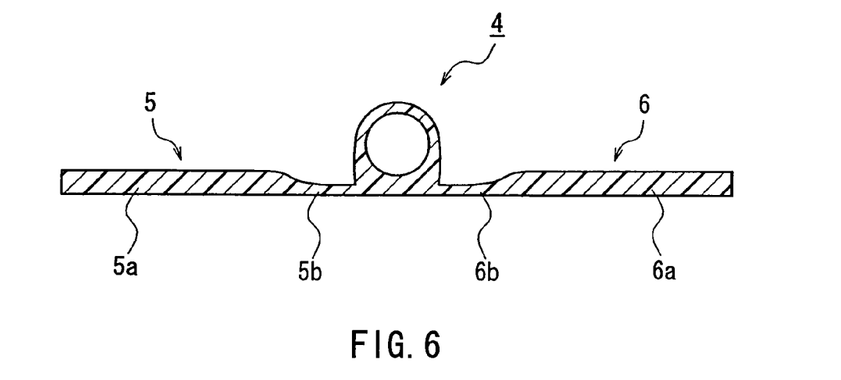
FIG. 6 is a cross-sectional view taken on line C-C' of FIG. 2.

FIG. 6 is a cross-sectional view taken on line C-C' of FIG. 2. As shown in FIG. 6, the wings 5 and 6 include front-end-side regions 5a and 6a and base-end-side regions (regions on the side where the wings 5 and 6 are linked to the shield tube 4a) 5b and 6b. The thickness of the base-end-side regions 5b and 6b is smaller than the thickness of the front-end-side regions 5a and 6a. Thus, the wings 5 and 6 can be bent easily at the base-end-side regions 5b and 6b.

Figure 7:
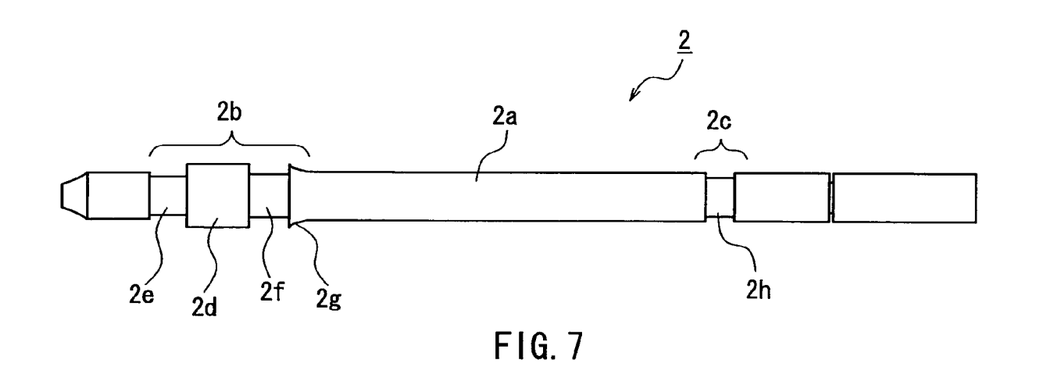
FIG. 7 is a plan view of a hub of the winged medical needle device shown in FIG. 1.
Figure 8:
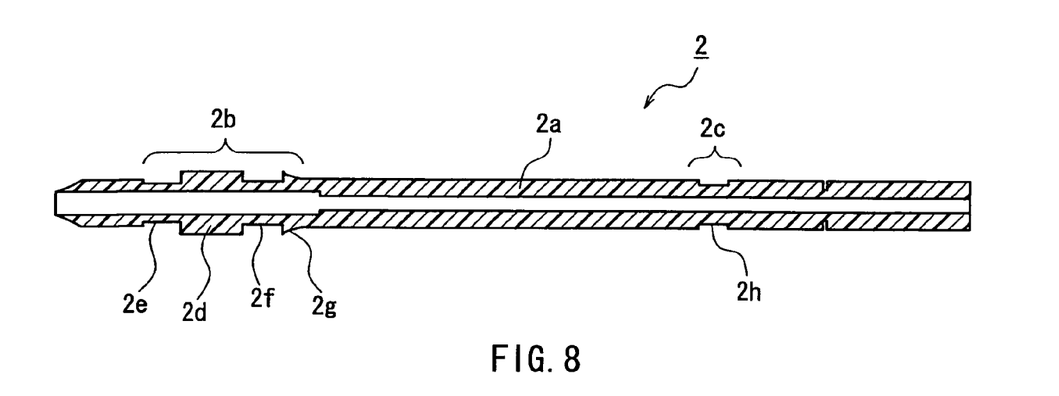
FIG. 8 is a cross-sectional view of the hub shown in FIG. 7 in the axial direction.

Next, the hub 2 that is used in combination with the winged shield 4 shown in FIGS. 2 to 6 is described with reference to FIGS. 7 and 8. FIG. 7 is a plan view showing the external shape of the hub 2, and FIG. 8 is a cross-sectional view thereof in the axial direction.

The hub 2 includes a main tubular portion 2a at a central portion in the axial direction, a first holding portion 2b that is provided on a side closer to the front end than the main tubular portion 2a, and a second holding portion 2c that is provided on a side closer to the rear end than the main tubular portion 2a. The outer diameter of the main tubular portion 2a of the hub 2 is smaller than the inner diameter of the shield tube 4a at a portion in which the inward annular protrusion 26 (see FIG. 5) is provided. Thus, in the state where the hub 2 is not held with the winged shield 4 by the holding mechanism, over the area in which the inward annular protrusion 26 faces the main tubular portion 2a, the hub 2 can be moved freely in the axial direction with respect to the shield tube 4a.

The first holding portion 2b provided at the front end portion of the hub 2 includes a first large diameter portion 2d, a first annular groove 2e, a second annular groove 2f, and a second large diameter portion 2g. The first large diameter portion 2d has a portion whose diameter is larger than the diameter of the main tubular portion 2a. The first annular groove 2e is provided on a side closer to the front end of the hub 2 than the first large diameter portion 2d so as to be adjacent to the first larger diameter portion 2d. The second annular groove 2f is provided on a side closer to the rear end than the first larger diameter portion 2d. The second large diameter portion 2g is provided on a side closer to the rear end than the second annular groove 2f so as to be adjacent to the second annular groove 2f. The maximum outer diameter of the second large diameter portion 2g is slightly larger than the inner diameter of the shield tube 4a at a portion in which the inward annular protrusion 26 (see FIG. 5A) is provided. It is preferable that the first large diameter portion 2d has an outer diameter larger than the maximum outer diameter of the second large diameter portion 2g. With the outer diameter of the first large diameter portion 2d that is larger than the maximum outer diameter of the second large diameter portion 2g, even when a force by which the hub is moved toward the base end of the shield tube is applied to the hub or the like in the state where the inward annular protrusion 26 (see FIG. 5A) is engaged with the second annular groove, the inward annular protrusion 26 is caught securely by the first large diameter portion 2d.

Figure 9:
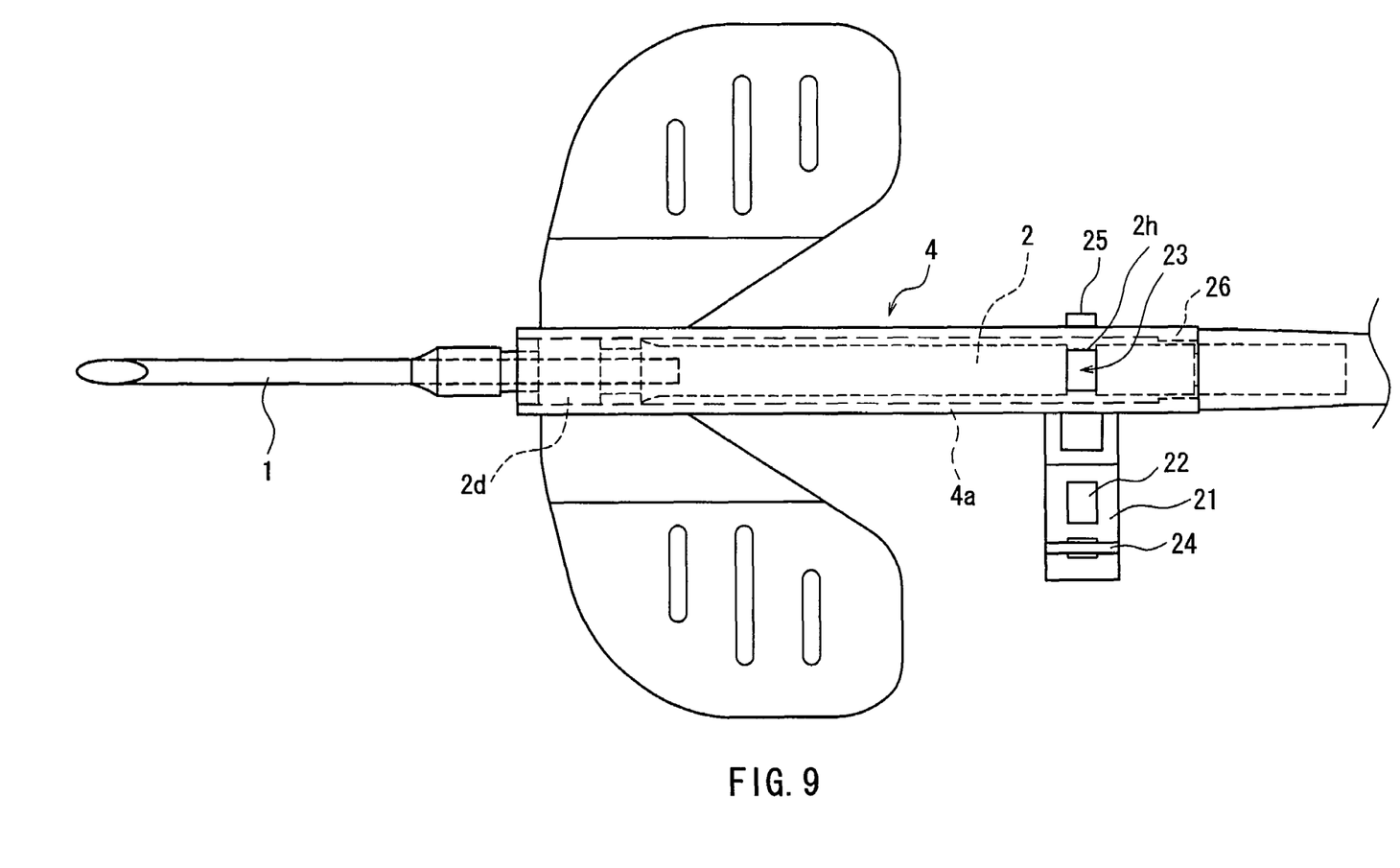
FIG. 9 is a plan view of the winged medical needle device according to Embodiment 1 of the present invention.

The second holding portion 2c provided on the rear end side of the hub 2 includes the third annular groove 2h. As shown in FIG. 9, in the state where the hub 2 is inserted into the shield tube 4a so that the cannula 1 protrudes for a predetermined length from the front end side of the shield tube 4a, the third annular groove 2h is positioned so as to correspond to the position of the through hole 23 provided on the shield tube 4a.

When inserting the hub 2 into the winged shield 4, as shown in FIG. 9, initially, the latching between the protruding piece portion 24 provided on the bendable strip 21 and the latching protrusion 25 provided on the shield tube 4a is released so as to obtain a state where the protrusion 22 is not inserted into the through hole 23. Next, the hub 2 is inserted from the front end side of the shield tube 4a and moved to the base end side of the shield tube 4a. The timing of connecting the tube 3 to the hub 2 may be before or after the hub 2 is inserted into the shield tube 4a.

A winged medical needle device in the state shown in FIG. 1 is obtained in the above-mentioned manner. In FIG. 1, the hub 2 is in its usage position. In this state, by wrapping the bendable strip 21, the protrusion 22 is inserted into the through hole (see FIG. 9) so that the protrusion 22 is engaged with the third annular groove 2h, and the protruding piece portion 24 is latched to latching protrusion 25. By these actions, a holding force for holding the hub 2 with the winged shield 4 can be applied. The movement of the hub 2 in the axial direction within the shield tube 4a is inhibited, and thus a state where the hub 2 is held in the shield tube 4a is obtained. The cannula 1 is kept from protruding more than a predetermined length from the shield tube 4a. In this case, it is preferable that the hub 2 is rotatable around the center axis of the hub 2 in the shield tube 4a.

The holding force applied to the hub 2 in the state where the cannula 1 protrudes for a predetermined length from the front end side of the shield tube 4a helps to avoid accidents caused when the cannula 1 is applied to the patient and then retained. Such accidents include a case where the cannula 1 is moved toward the base end of the winged shield 4 and removed from the patient.

Figure 12:
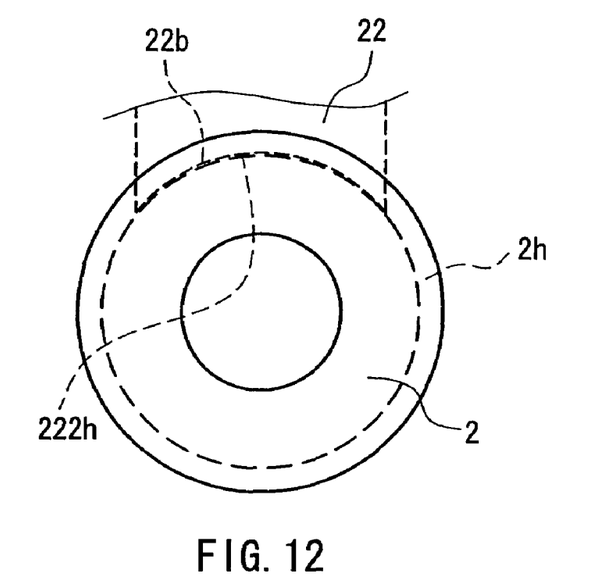
FIG. 12 is a cross-sectional view of the hub, which is cut in a direction orthogonal to the axis of the hub, of the winged medical needle device according to. Embodiment 1 of the present invention.

FIG. 12 is a cross-sectional view of the hub that is cut in a direction orthogonal to the axis of the hub for explaining the state where the hub is engaged with the protrusion of the holding mechanism. In FIG. 12, the hub in cross section is shown without hatching so as not to be complicated.

As shown in FIG. 12, preferably, a surface 22b of the protrusion 22 that faces a bottom surface 222h of the third annular groove 2h when the protrusion 22 is engaged with the third annular groove 2h includes a curved surface having a curvature equal to the curvature of the bottom surface 222h of the third annular groove 2h. This is preferable because, for example, even in the case where the surface 22b of the protrusion 22 faces the above-mentioned bottom surface 222h over a relatively large area, the hub 2 can be rotated easily within the shield tube. Thus, before the cannula 1 is set into the patient's body, an aperture 1a (see FIG. 1) at the tip of the cannula 1 easily can be set in a predetermined orientation. Further, this also facilitates the action of changing the orientation of the aperture 1a (see FIG. 1), which is performed as required after the cannula 1 has been inserted into a bloodvessel of the patient. In order to allow the hub 2 to be rotated easily within the shield tube, the curvature of the abovementioned curved surface of the surface 22b does not have to be exactly the same but is only required to be substantially the same as that of the bottom surface 222h.

On the other hand, when disposing of the winged medical needle device after use, in order to prevent needle-stick injuries, the tip of the cannula 1 is stored in the shield tube 4a. In this case, the hub 2 is moved toward the base end of the shield tube 4a. This action is hindered if the holding force for holding the hub 2 with the winged shield is too large. In this embodiment, by releasing holding by the holding mechanism, the cannula 1 after use can be stored easily in the shield tube 4a. Specifically, latching by a latching structure is released, and the engagement between the protrusion 22 of the bendable strip 21 and the third annular groove 2h is released.

When holding by the holding mechanism is released and the hub 2 in the state shown in FIG. 1 is moved toward the base end of the shield tube 4a, since the maximum outer diameter of the second large diameter portion 2g is larger than the inner diameter of the shield tube 4a at a portion in which the inward annular protrusion 26 is provided, firstly, the inward annular protrusion 26 comes into contact with the second large diameter portion 2g. The second large diameter portion 2g has a slope on the rear side thereof, and moreover, its maximum outer diameter is only slightly larger than the inner diameter of the inward annular protrusion 26. Therefore, by forcefully moving the hub 2 further, the inward annular protrusion 26 easily can pass over the second large diameter portion 2g.

Figure 10:
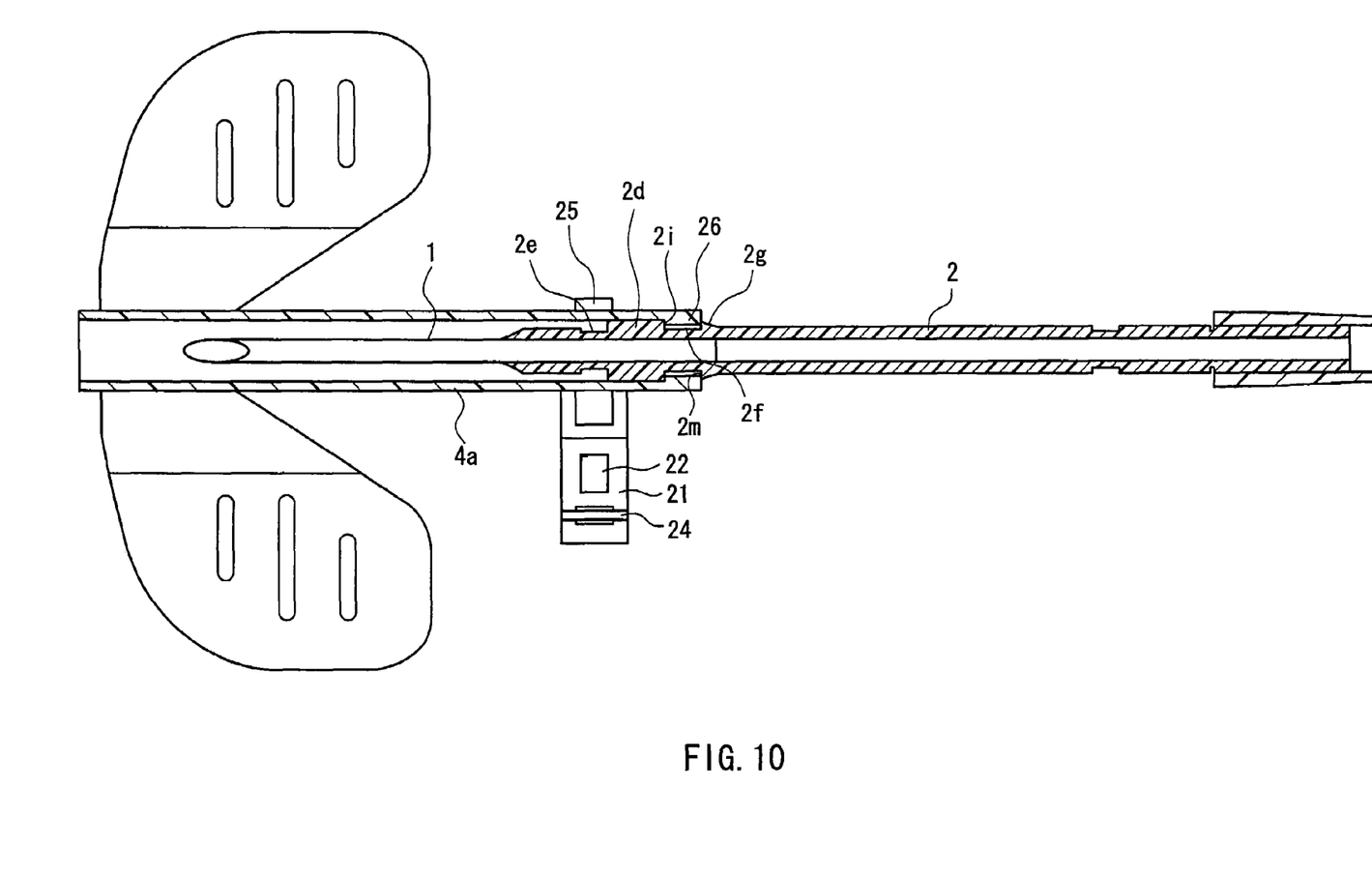
FIG. 10 is a partial cross-sectional view showing the operation of the winged medical needle device shown in FIG. 1.

As shown in FIG. 10, after passing over the second large diameter portion 2g, the inward annular protrusion 26 is engaged with the second annular groove 2f. The inward annular protrusion 26 that has passed over the second large diameter portion 2g hinders a movement toward the rear end of the hub 2 by engaging a step portion 2m formed on the outer surface of the second large diameter portion 2g. Further, the inward annular protrusion 26 that has passed over the second large diameter portion 2g also hinders a movement toward the front end of the hub 2 by engaging a step portion 2i formed on the rear outer surface of the first large diameter portion 2d.

The tip of the cannula 1 is stored in the shield tube 4a in this manner, thereby obtaining a state where needle-stick injuries are avoided. A large force by which the shield tube 4a is moved toward the rear end of the hub 2 may be applied erroneously to the shield tube 4a or the like, and thus the inward annular protrusion 26 may pass over the second large diameter portion 2g, causing the cannula 1 to protrude from the front end side of the shield tube 4a. In order to avoid this, the winged medical needle device according to this embodiment includes the following safety mechanism. That is, when the protrusion 22 provided on the bendable strip 21 is inserted into the through hole 23 (see FIG. 9) and the protruding piece portion 24 is latched to the latching protrusion 25, the state of engagement between the protrusion 22 and the first annular groove 2e is maintained securely, and the hub 2 is held securely with the winged shield 4 so that it cannot move toward either the front end or the base end of the shield tube 4e.

Figure 11:
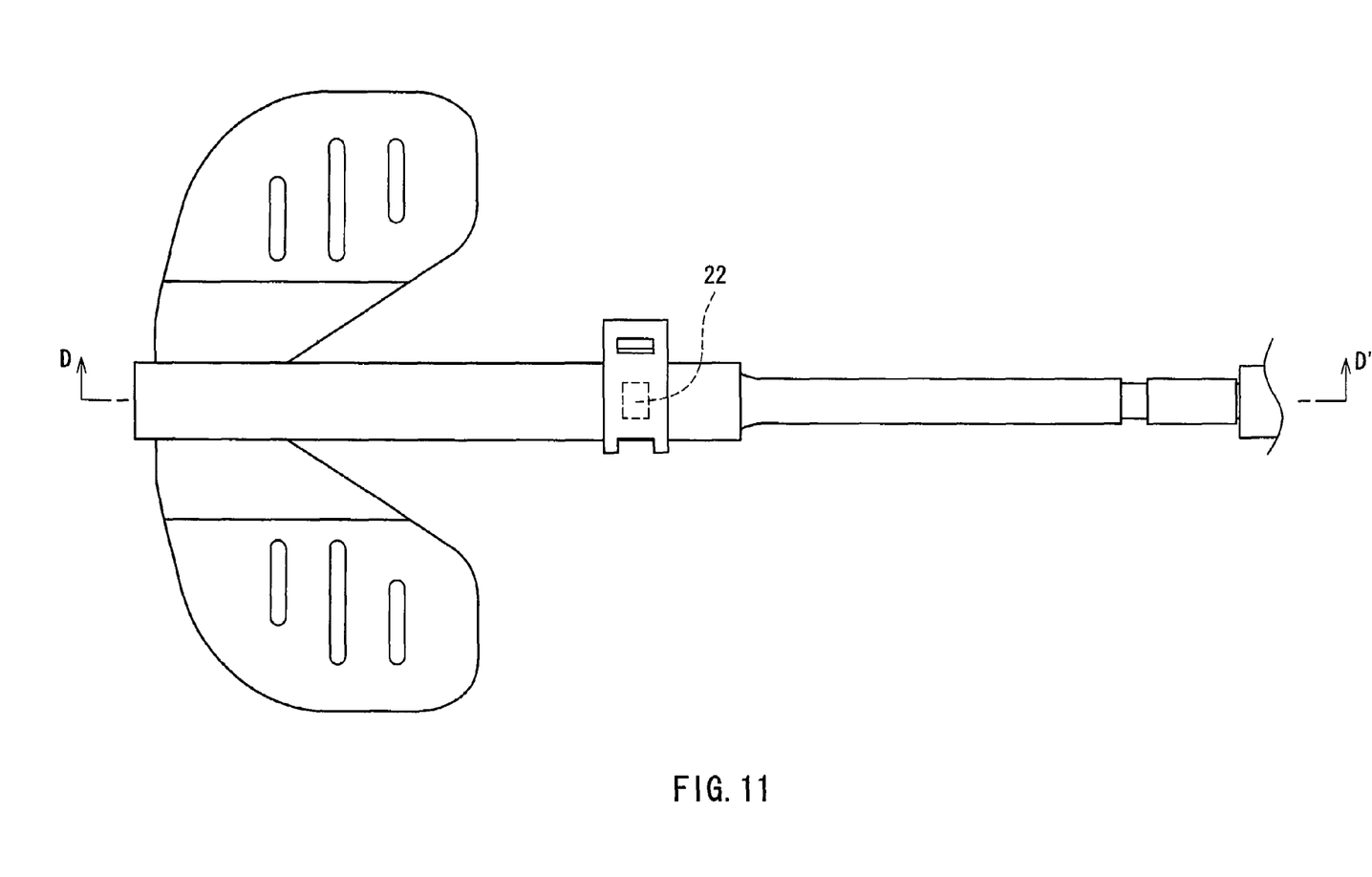
FIG. 11 is a plan view showing the winged medical needle device shown in FIG. 10.
Figure 13:
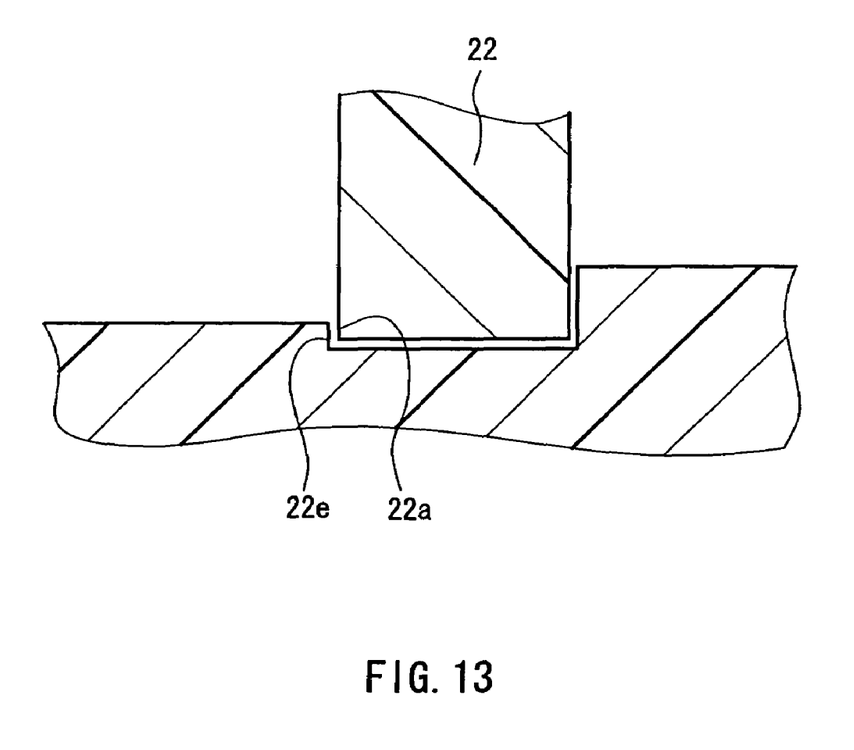
FIG. 13 is an expanded cross-sectional view taken on line D-D' of FIG. 11 for showing the hub and the protrusion of a holding mechanism.

FIG. 11 shows the state where the protrusion 22 is engaged with the first annular groove. FIG. 13 is a cross-sectional view taken on line D-D' of FIG. 11 for showing only the hub and the protrusion of the holding mechanism.

As shown in FIG. 13, a surface 22a of the protrusion 22 that faces a side surface 22e of the first annular groove 2e on the front end side when the protrusion 22 is engaged with the first annular groove 2e includes a plane surface. There is no particular limit to the shape of the protrusion 22, and the protrusion 22 may have a hemispherical shape or the like as long as the protrusion 22 can be engaged with the first annular groove 2e and the third annular groove 2h. With the above-mentioned surface 22a being a plane surface, for example, compared with the case where the protrusion 22 is hemispherical, the surface of the protrusion 22 can come into contact with the side surface 22e in a larger area. Thus, for example, compared with the case where the protrusion 22 is hemispherical, the holding force for holding the hub 2 with the winged shield can be increased.

In this embodiment, the engagement between the protrusion 22 and the first annular groove 2e or the third annular groove 2h is maintained by the latching structure including the protruding piece portion and the latching protrusion. However, the present invention is not limited thereto. For example, if the shape of the protrusion 22 or a through hole into which the protrusion 22 is inserted is set appropriately so that the protrusion 22 is press-fitted into the through hole, the following can be achieved. That is, even in the case where the holding mechanism does not have the latching structure composed of the protruding piece portion and the latching protrusion, the state of engagement between the protrusion 22 and the first annular groove 2e or the third annular groove 2h can be maintained, and a holding force also can be applied to the hub 2.

It is preferable that the shape of the inner bore of the shield tube 4a corresponds to the shape of the outer surface of the hub 2. For example, if the hub 2 has a circular cross section perpendicular to its axis, it is preferable that the inner bore of the shield tube 4a is circular, or that at least a portion of the inner bore is circular. In this embodiment, the inner bore of the shield tube 4a is circular. However, the inner bore also may be of a configuration in which the upper side of the inner bore is formed as a curved surface, and the bottom portion of the inner bore surface is flat (see FIGS. 3 and 4). It is preferable that the bottom portion of the outer surface of the shield 4a is made flat so as to be placed stably on the patient's skin.

Needless to say, it is required that the shield tube 4a have a length sufficient to allow the tip of the cannula 1 to be stored completely.

It is preferable that the inner bore of the shield tube 4a (except for a portion in which the inward annular protrusion 26 is provided) has a diameter that is substantially equal to the maximum outer diameter of the hub 2, and it is more preferable that the diameter is slightly larger than the maximum outer diameter of the hub 2. In this case, the hub 2 can be moved easily in the axial direction of the inner bore of the shield tube.

Next, the description is directed to a method of using the winged medical needle device according to the above-described embodiment.

For use, as shown in FIG. 1, the hub 2 to which the cannula 1 has been attached is inserted into the winged shield 4, and the winged medical needle device is made available with the tube 3 connected to the hub 2. The hub 2 is held with the winged shield 4 in the state where the cannula 1 protrudes for a predetermined length from the shield tube 4a. In this case, the hub 2 is held with the winged shield 4 by means of the holding mechanism and the second holding portion (third annular groove 2h). Specifically, the opening of the protruding piece portion 24 of the bendable strip 21 is latched to the latching protrusion 25 provided on the shield tube 4a, and thus the state of engagement between the protrusion 22 and the third annular groove 2h is maintained, thereby allowing the hub 2 to be held with the winged shield 4.

While holding the two wings 5 and 6 together with one hand, the practitioner removes the needle cap 18 from the cannula 1 with the other hand. In this state, the cannula 1 is inserted into the patient's body.

When the cannula 1 has been set on the patient, the two wings 5 and 6 that had overlapped each other are spread apart, and are fastened on the patient's skin, for example, with adhesive tape. In this state, the hub 2 is held with the winged shield 4 by means of the holding mechanism and the second holding portion (third annular groove 2h). This avoids a situation in which the cannula 1 is moved in the axial direction toward the base end within the shield tube 4a and removed from the patient's body.

When the infusion of a drug solution or the like into the patient's body has been finished, the latching between the protruding piece portion 24 and the latching protrusion 25 is released, and the engagement between the protrusion 22 and the third annular groove 2h is released, so that the hub 2 can be moved. Then, the tube 3 is pulled toward the base end of the shield tube 4a with the wings 5 and 6 still fastened in place or pressed down by hand. When the tube 3 is pulled toward the base end of the shield tube 4a, the inward annular protrusion 26 is engaged with the second annular groove 2f, and at the same time, the tip of the cannula 1 is stored in the shield tube 4, thereby obtaining a state where needle-stick injuries are avoided. Moreover, the protrusion 22 provided on the bendable strip 21 is engaged with the first annular groove 2e, and the protruding piece portion 24 provided on the bendable strip 21 is latched to the latching protrusion 25 provided on the shield tube 4a, thereby maintaining the state of engagement between the protrusion 22 and the first annular groove 2e. These actions allow the hub 2 to be held securely with the winged shield so as not to be moved within the shield tube 4a.

Figure 14:
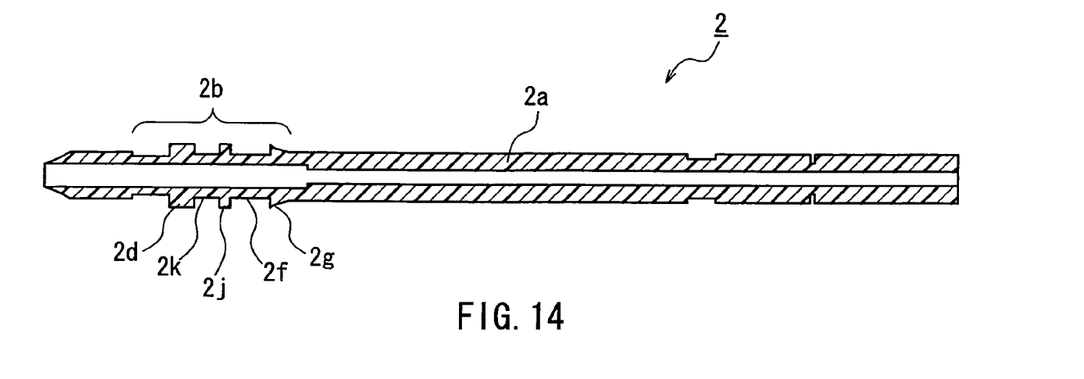
FIG. 14 is a cross-sectional view of a hub of another type, which is taken in the axial direction, of the winged medical needle device according to Embodiment 1 of the present invention.

FIG. 14 is a cross-sectional view of a hub 2 of another type, which is taken in the axial direction, of the winged medical needle device according to this embodiment. In the hub 2 shown in FIG. 14, in addition to the configuration of the hub 2 shown in FIGS. 7 and 8, a third large diameter portion 2j further is provided between the first large diameter portion 2d and the second annular groove 2f, and a fourth annular groove 2k is formed between the first large diameter portion 2d and the third large diameter portion 2j.

In this case, in order to prevent the inward annular protrusion 26 (see FIG. 5A) from passing over the third large diameter portion 2j, it is preferable that the third large diameter portion 2j has an outer diameter larger than the maximum outer diameter of the second large diameter portion. With the outer diameter of the third large diameter portion 2j that is larger than the maximum outer diameter of the second large diameter portion 2g, even when a force by which the hub is moved in the base end direction of the shield tube is applied to the hub or the like in the state where the inward annular protrusion is engaged with the second annular groove 2f, the inward annular protrusion 26 is caught securely by the third large diameter portion 2j.

Figure 15:
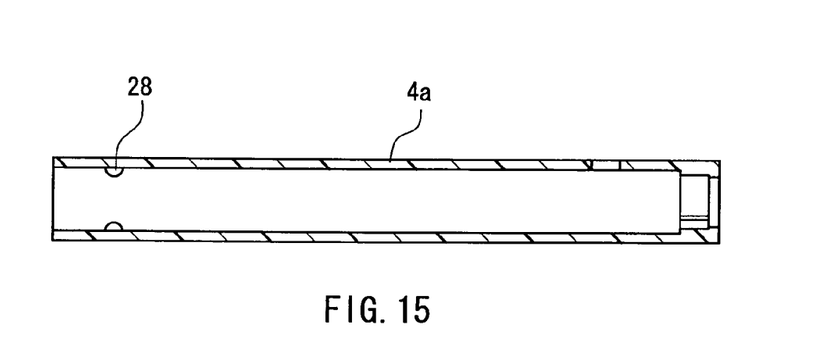
FIG. 15 is a cross-sectional view in an axial direction of another winged shield of the winged medical needle device shown in FIG. 1.

In the case where the first holding portion 2b includes the third large diameter portion 2j and the fourth annular groove 2k as described above, it is preferable that, as shown in FIG. 15, the inner surface of the shield tube 4a is provided with an auxiliary holding protrusion 28. There is no particular limit to the shape of the auxiliary holding protrusion 28, and the auxiliary holding protrusion 28 may have a hemispherical shape or the like. There is also no particular limit the number of the auxiliary holding protrusion 28 as long as the number is not lower than one. For example, it is preferable that, shown in FIG. 15, two auxiliary holding protrusions 28 are arranged so as to be symmetrical with respect to the axis of the shield tube. In the state where positioning between the through hole 23 and the third annular groove is obtained so that the protrusion 22 (see FIG. 1) of the bendable strip can be engaged with the third annular groove 2h, the auxiliary holding protrusion 28 is positioned in the axial direction so as to correspond to the position of the fourth annular groove 2k (see FIG. 14). With the inner surface of the shield tube 4a being provided with the above-mentioned auxiliary holding protrusion 28, in the case where the hub is not held by the holding mechanism in the state where the cannula protrudes for a predetermined length from the front end of the shield tube 4a, a free movement of the shield tube can be restricted.

Furthermore, in the case where the first holding portion 2b (see FIG. 14) includes the third large diameter portion 2j and the fourth annular groove 2k, it is preferable that the inner bore of the shield tube (except for a portion in which the inward annular protrusion is provided) has a diameter that is slightly larger than either of the respective outer diameters of the first large diameter portion 2d, the second large diameter portion 2g, and the third large diameter portion 2j. In this case, the hub 2 can be moved easily in the axial direction of the inner bore of the shield tube.

Embodiment 2

Figure 16:
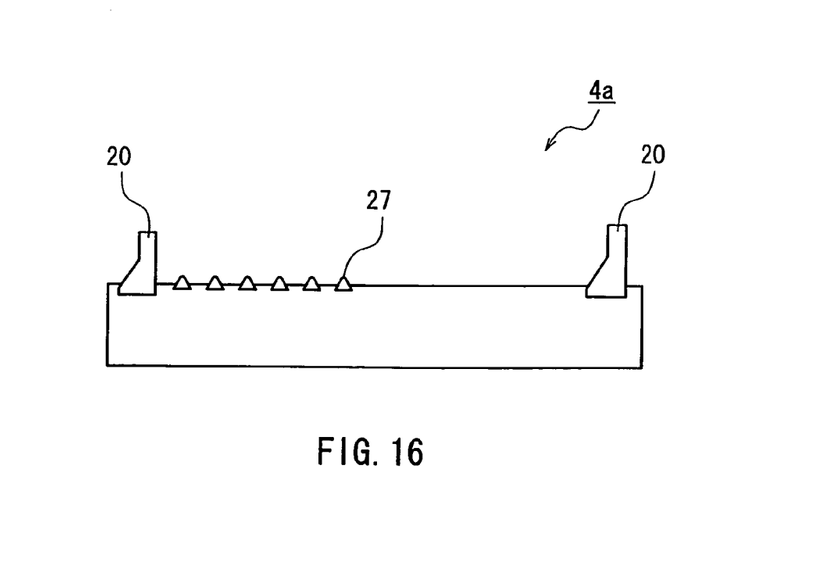
FIG. 16 is a side view of a shield tube of a winged medical needle device according to Embodiment 2 of the present invention.

FIG. 16 shows a shield tube of a winged medical needle device according to Embodiment 2. In the winged medical needle device according to this embodiment, in addition to the configuration of Embodiment 1, a holding tab 20 is provided at the upper surface of the shield tube 4a. As described above, after using the winged medical needle device, the tube connected to the hub is pulled toward the base end of the shield tube 4a, and the hub is held inside the shield tube 4a in the state where needle-stick injuries can be avoided. For this, the holding tab 20 is used to fasten the shield tube 4a so that it is not moved. That is, by placing a finger on the holding tab 20 and countering the force pulling the tube, the action of pulling the hub toward the base end of the shield tube 4a is facilitated. It is preferable that the holding tub 20 is formed at the front end portion of the shield tube 4a, particularly, on a side closer to the front end than the wings (see FIG. 1). With the holding tab 20 provided on the front end portion of the shield tub 4a, when performing the action of pulling the hub toward the base end of the shield tube 4a, it is made easier to fasten the shield tube 4a so that it is not moved from a predetermined position by pressing down the wings as well as the shield tube 4a from above. Thus, the action of pulling the hub toward the base end of the shield tube 4a is facilitated further. In order for the practitioner to avoid touching the front end side of the shield tube 4a, which is close to the cannula 1, the holding tab 20 also may be provided at the rear end portion of the shield tube 4a.

Furthermore, in the winged medical needle device according to the present invention, anti-slip protrusions 27 are provided on the upper portion of the outer surface of the shield tube 4a, thereby achieving improved handling ease of the winded shield.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A winged medical needle device, comprising:
a winged shield that has a substantially cylindrical shield tube and a pair of wings linked to a front end side of the shield tube;
a hub that is inserted into an inner bore of the shield tube so as to be movable in an axial direction; and
a cannula that is mounted to a front end portion of the hub,
wherein the hub includes a main tubular portion, a first holding portion that is provided on a side closer to a front end than the main tubular portion, and a second holding portion that is provided on a side closer to a rear end than the main tubular portion,
the first holding portion includes a first large diameter portion that has a portion whose diameter is larger than a diameter of the main tubular portion, a first annular groove that is provided on a side closer to the front end of the hub than the first large diameter portion, a second annular groove that is provided on a side closer to the rear end than the first large diameter portion, and a second large diameter portion that is provided on a side closer to the rear end than the second annular groove so as to be adjacent to the second annular groove,
the second holding portion includes a third annular groove,
the winged shield includes a holding mechanism that is provided at a base end portion of the shield tube, and an inward annular protrusion that is formed on an inner surface of the shield tube on a side closer to a base end than the holding mechanism, and the inward annular protrusion can be engaged with the second annular groove,
the holding mechanism includes a bendable strip that is attached to an outer peripheral surface of the shield tube, a protrusion that is provided on the bendable strip, and a through hole that is provided on a wall of the shield tube so that the protrusion can be inserted into the inner bore of the shield tube by wrapping of the bendable strip, and the protrusion can be engaged with the first annular groove and the third annular groove,
by inserting the protrusion into the through hole so that the protrusion is engaged with the third annular groove, the hub is held with the shield tube so as not to be moved within the shield tube in a state where the cannula protrudes for a predetermined length from a front end of the shield tube,
a surface of the protrusion that faces a bottom surface of the third annular groove when the protrusion is engaged with the third annular groove is a curved surface having a curvature substantially equal to a curvature of the bottom surface and is in contact with the bottom surface of the third annular groove, and
by moving the hub in the axial direction toward the base end with respect to the shield tube, the inward annular protrusion of the shield tube is engaged with the second annular groove of the hub, and a tip of the cannula is stored in the shield tube in this state, and further by engaging the protrusion of the holding mechanism with the first annular groove, the hub is held with the shield tube so as not to be moved within the shield tube; and
by inserting the protrusion into the through hole so that the protrusion is engaged with the third annular groove, the hub is held so as not be moved while being rotatable within the shield tube in the state where the cannula protrudes for a predetermined length from the front end of the shield tube.

2. The winged medical needle device according to claim 1,
wherein the holding mechanism further includes a latching structure that allows the bendable strip to be latched to the shield tube.

3. The winged medical needle device according to claim 2,
wherein the latching structure includes a latching protrusion that is provided on the outer peripheral surface of the shield tube, and a protruding piece portion that is provided on a front end side of the bendable strip and includes an opening.

4. The winged medical needle device according to claim 1,
wherein the first holding portion further includes a third large diameter portion that is arranged between the first large diameter portion and the second annular groove, and a fourth annular groove that is arranged between the first large diameter portion and the third large diameter portion, and
the inner surface of the shield tube is provided with an auxiliary holding protrusion that is formed in a position of the inner surface of the shield tube, in which the auxiliary holding protrusion faces the fourth annular groove when positioning between the through hole and the third annular groove is obtained so that the protrusion provided on the bendable strip can be engaged with the third annular groove.

5. The winged medical needle device according to claim 4,
wherein the third large diameter portion has an outer diameter larger than a maximum outer diameter of the second large diameter portion.

6. The winged medical needle device according to claim 1,
wherein a holding tab is formed on an upper surface of the shield tube.

7. The winged medical needle device according to claim 6,
wherein the holding tab is formed on at least one selected from a front end portion of the shield tube and a rear end portion of the shield tube.

8. The winged medical needle device according to claim 1,
wherein the first large diameter portion has an outer diameter larger than a maximum outer diameter of the second large diameter portion.

9. The winged medical needle device according to claim 1,
wherein a surface of the bendable strip that faces an outer surface of the shield tube when the protrusion is engaged with the third annular groove includes a curved surface having a curvature substantially equal to a curvature of the outer surface.

10. The winged medical needle device according to claim 1,
wherein a surface of the protrusion that faces a side surface of the first annular groove on a front end side of the first annular groove when the protrusion is engaged with the first annular groove includes a plane surface.

11. The winged medical needle device according to claim 1,
wherein a surface of the inward annular protrusion is provided with a rib parallel to the axial direction of the shield tube and a rearward annular protrusion that is arranged on a side closer to the base end than the rib, and
the rib has a length in a longitudinal direction that is longer than a width of the third annular groove.

12. The winged medical needle device according to claim 1,
wherein the pair of wings have a thickness that is smaller in a region on a base end side than in a region on a front end side.

13. The winged medical needle device according to claim 1,
wherein an outer surface of a bottom portion of the shield tube is formed so as to be flat.

14. A winged medical needle device, comprising:
a winged shield that has a substantially cylindrical shield tube and a pair of wings linked to a front end side of the shield tube;
a hub that is inserted into an inner bore of the shield tube so as to be movable in an axial direction; and
a cannula that is mounted to a front end portion of the hub,
wherein the hub includes a main tubular portion, a first holding portion that is provided on a side closer to a front end than the main tubular portion, and a second holding portion that is provided on a side closer to a rear end than the main tubular portion,
the first holding portion includes a first large diameter portion that has a portion whose diameter is larger than a diameter of the main tubular portion, a first annular groove that is provided on a side closer to the front end of the hub than the first large diameter portion, a second annular groove that is provided on a side closer to the rear end than the first large diameter portion, and a second large diameter portion that is provided on a side closer to the rear end than the second annular groove so as to be adjacent to the second annular groove,
the second holding portion includes a third annular groove,
the winged shield includes a holding mechanism that is provided at a base end portion of the shield tube, and an inward annular protrusion that is formed on an inner surface of the shield tube on a side closer to a base end than the holding mechanism, and the inward annular protrusion can be engaged with the second annular groove,
the holding mechanism includes a bendable strip that is attached to an outer peripheral surface of the shield tube, a protrusion that is provided on the bendable strip, and a through hole that is provided on a wall of the shield tube so that the protrusion can be inserted into the inner bore of the shield tube by wrapping of the bendable strip, and the protrusion can be engaged with the first annular groove and the third annular groove,
by inserting the protrusion into the through hole so that the protrusion is engaged with the third annular groove, the hub is held with the shield tube so as not to be moved within the shield tube in a state where the cannula protrudes for a predetermined length from a front end of the shield tube,
a surface of the protrusion that faces a bottom surface of the third annular groove when the protrusion is engaged with the third annular groove is a curved surface having a curvature substantially equal to a curvature of the bottom surface,
by moving the hub in the axial direction toward the base end with respect to the shield tube, the inward annular protrusion of the shield tube is engaged with the second annular groove of the hub, and a tip of the cannula is stored in the shield tube in this state, and further by engaging the protrusion of the holding mechanism with the first annular groove, the hub is held with the shield tube so as not to be moved within the shield tube, and
a surface of the inward annular protrusion is provided with a rib parallel to the axial direction of the shield tube and a rearward annular protrusion that is arranged on a side closer to the base end that the rib, the rib has a length in a longitudinal direction that is longer that a width o the third annular groove, and the surface of the inward annular protrusion at a portion where the rib is joined to the rearward annular protrusion is a plane surface.

15. The winged medical needle device according to claim 14, wherein a portion of the surface of the inward annular protrusion on a side closer to the front end than the rearward annular protrusion is slanted, and the shield tube has an inner diameter at a portion in which the inward annular protrusion is provided, which increases from the base end to the front end on the side closer to the front end than the rearward annular protrusion.

* * * * *